United States Patent
Machesky (10) Patent No.: US 11,740,230 B2
(45) Date of Patent: Aug. 29, 2023

(54) CELL-BASED ASSAY USING ELECTROPHYSIOLOGICAL ACTIVITY MEASURED WITH MICROELECTRODE ARRAYS

(71) Applicant: Battelle Memorial Institute, Columbus, OH (US)

(72) Inventor: Nicholas J. Machesky, Dublin, OH (US)

(73) Assignee: Batelle Memorial Institute, Columbus, OH (US)

( * ) Notice: Subject to any disclaimer, the term of this patent is extended or adjusted under 35 U.S.C. 154(b) by 664 days.

(21) Appl. No.: 16/813,053

(22) Filed: Mar. 9, 2020

(65) Prior Publication Data
US 2020/0292530 A1 Sep. 17, 2020

Related U.S. Application Data (60) Provisional application No. 62/817,303, filed on Mar. 12, 2019.

(51) Int. Cl.
*G01N 33/50* (2006.01)

(52) U.S. Cl.
CPC ..... *G01N 33/5058* (2013.01); *G01N 33/5014* (2013.01); *G01N 2333/33* (2013.01)

(58) Field of Classification Search
None
See application file for complete search history.

(56) References Cited

U.S. PATENT DOCUMENTS

2015/0362482 A1 12/2015 McNutt et al.

OTHER PUBLICATIONS

Machesky, Nicholas J. et al., A Cell-Based BoNT Potency Assay using Electrophysiological Activity Measured with Microelectrode Arrays, presented at the 57th Annual Meeting of the Society of Toxicology (SOT 2018) held in San Antonio, TX on Mar. 13, 2018.
Jenkinson et al., Embryonic Stem Cell-Derived Neurons Grown on Multi-Electrode Arrays as a Novel In vitro Bioassay for the Detection of Clostridium botulinum Neurotoxins, Frontiers in Pharmacology, Feb. 2017, vol. 8, Article 73, www.frontiersin.org.
Pancrazio, Joseph J. et al., Botulinum Toxin Suppression of CNS Network Activity In Vitro, Journal of Toxicology, Feb. 12, 2014, vol. 2014, Article ID 732913, Hindawi Publishing Corporation.
Beske, Dr. Phillip H., et al., Function-based screening of botulinum neurotoxin countermeasures with multi-well microelectrode arrays, Science and Mathematics Academy, 2017, http://www.scienceandmathacademy.com/academics/srt4/student_work/2017/cerasoli_mark.pdf.
Bradley, Jenifer A., et al., Screening for Neurotoxicity with Microelectrode Array, Current Protocols in Toxicology, 2019, vol. 79, e67.
Quasthoff, Kim et al., Freshly frozen E18 rat cortical cells can generate functional neural networks after standard cryopreservation and thawing procedures, Cytotechnology, Feb. 23, 2014, pp. 419-426, vol. 67.
Scarlatos, Amber Christine, Random Cortical Networks Grown On Microelectrode Arrays As Cell-Based Biosensors For Neurotoxins As Demonstrated By Botulinum Toxin Type A, University of Florida Dissertation, University of Florida, 2007.
Black, Bryan J., Spontaneous and Evoked Activity from Murine Ventral Horn Cultures on Microelectrode Arrays, Frontiers in Cellular Neuroscience, Sep. 29, 2017, vol. 11, art. 304.
Beske, Dr. Phillip H., et al., Botulinum and Tetanus Neurotoxin-Induced Blockade of Synaptic Transmission in Networked Cultures of Human and Rodent Neurons, Toxicological Sciences, Society of Toxicology, 2016, vol. 149, No. 2, pp. 503-515.

*Primary Examiner* — Brian Gangle
(74) *Attorney, Agent, or Firm* — Lippes Mathias LLP (57) ABSTRACT

Methods for detecting and/or quantifying the potency of an agent using a cell-based assay are disclosed. A mammalian cell culture is grown upon a microelectrode array (MEA) which is used to measure an electrophysiological response of the mammalian cell culture. The cell culture is exposed to the agent, generally in at least two different dosages. The potency of the agent is detected by measuring a change in the electrophysiological responses associated with the at least two dosages when compared to a control condition. These changes can include the weighted mean firing rate (wMFR) and bursting of the cells.

16 Claims, 4 Drawing Sheets

**Fresh Primary Rat Brain Neurons
Weighted Mean Firing Rate**

A  Media Control
B  50 pM Pure BoNT/A
C  5.0 pM Pure BoNT/A
D  50 pM Pure BoNT/A
E  500 pM Pure BoNT/A
*  = $p < 0.05$

FIGURE 3A

**Fresh Primary Rat Brain Neurons
Number of Bursts**

A  Media Control
B  50 pM Pure BoNT/A
C  5.0 pM Pure BoNT/A
D  50 pM Pure BoNT/A
E  500 pM Pure BoNT/A
*  = $p < 0.05$

FIGURE 3B

Frozen Primary Rat Brain Neurons Weighted Mean Firing Rate

A Media Control
B 50 pM Pure BoNT/A
C 5.0 pM Pure BoNT/A
D 50 pM Pure BoNT/A
E 500 pM Pure BoNT/A
* = $P < 0.05$

FIGURE 4A

Frozen Primary Rat Brain Neurons Number of Bursts

A Media Control
B 50 pM Pure BoNT/A
C 5.0 pM Pure BoNT/A
D 50 pM Pure BoNT/A
E 500 pM Pure BoNT/A
* = $P < 0.05$

FIGURE 4B

CELL-BASED ASSAY USING ELECTROPHYSIOLOGICAL ACTIVITY MEASURED WITH MICROELECTRODE ARRAYS

This application claims the benefit of U.S. Provisional Patent Application Ser. No. 62/817,303 filed Mar. 12, 2019 and titled "CELL-BASED ASSAY USING ELECTROPHYSIOLOGICAL ACTIVITY MEASURED WITH MICROELECTRODE ARRAYS", which is incorporated herein by reference in its entirety.

BACKGROUND

The present disclosure relates to cell-based assays, methods for detecting the presence of an agent, and to methods for determining/quantifying the potency of an agent using such cell-based assays. The present disclosure describes particular applications of such cell-based arrays with respect to botulism neurotoxin (BoNT). However, it is to be appreciated that the present disclosure is also amenable to use in similar applications.

*Clostridium botulinum* neurotoxin (BoNT) is a poisonous, naturally occurring protein toxin that causes botulism—a severe and potentially life-threatening disease. There are seven known BoNT serotypes, labeled as serotypes A-G. Four of the serotypes (A, B, E and F) are associated with human illness—such as foodbourne botulism. Two BoNT serotypes (A and B) have found use in therapeutic applications. BoNT can be used as a pharmaceutical agent to treat a variety of neuromuscular disorders and chronic pain, as long as the potency of the BoNT is monitored to ensure the dosage does not reach toxic levels.

A number of approaches are currently employed to detect and quantify the functional effects of BoNT on neurons. The current approach for assessing the potency of botulinum toxin and antitoxins is a mouse lethality assay commonly known as the murine $LD_{50}$-assay. The murine $LD_{50}$-assay is an in vivo assay in which the test material is injected intraperitoneally or intravenously into mice until signs of toxicity (e.g., respiratory arrest) occur.

In vitro methods are being developed to reduce the need for such in vivo assays. Microelectrode array (MEA) systems enable a population of cells (known as a "network") to be cultured on an array of extracellular electrodes, which record extracellular voltage changes that occur during the firing of action potentials (spikes) across the network. Neurons may fire multiple action potentials within a short period of time, called a burst. The burst behavior can be used to characterize the functional effects of a toxin on neuronal signaling.

However, current cell-based assays have not proven to be as sensitive as the murine $LD_{50}$-assay. In other words, MEA networks respond similarly to different dosages of BoNT, making it difficult to detect the potency. In addition, for cultured neuronal networks exposed to BoNT, a rapid decay in electrical activity occurs after the exposure. Where stem cell-derived neurons are cultured on microelectrode arrays, a complete absence of neuronal activity is observed within twenty-four (24) hours after intoxication of the cells with BoNT/A. This causes problems in measuring the recovery of network activity after neurotoxin exposure.

Applications for employing an improved cell-based potency assay are widespread. Such assays could be used to detect the presence of a neurotoxic agent such as BoNT, determining a particular serotype of the agent, screening for neurotoxic agents, and measuring the efficacy of test treatments against the neurotoxic agent. Therefore, an in vitro assay is desired that can measure electrophysiological activity after a multiple-day exposure period. There is further desired a cell-based potency assay that has improved sensitivity in measuring electrophysiological activity within MEA cultures exposed to a neurotoxic agent.

BRIEF DESCRIPTION

The present disclosure relates to cell-based assays and methods for determining the effect of an agent on the biological activity of a mammalian cell culture. In this regard, methods are disclosed for measuring the potency of a neurotoxic agent (such as BoNT) by measuring the electrophysiological activity of a mammalian cell culture on a microelectrode array (MEA). Wells of the MEA are treated with at least two different dosage amounts ("dosages") or concentrations of the neurotoxic agent, which suppress electrophysiological activity from the mammalian cell culture. The potency of the neurotoxic agent can be measured by detecting the difference between the electrophysiological responses in wells exposed to dosages of the neurotoxic agent and control wells subjected to a media exchange. In some embodiments, the mammalian cell culture is sensitive to exposures at 0.50 pM BoNT, as evidenced by the number of bursts observed over one minute.

These and other non-limiting aspects of the present disclosure are described in more detail below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named components/steps and allowing the presence of other components/steps. The term "comprising" should be construed to include the term "consisting of", which allows the presence of only the named components/steps.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context. When used in the context of a range, the modifier "about" should also be considered as disclosing the range defined by the absolute values of the two endpoints. For example, the range of "from about 2 to about 10" also discloses the range "from 2 to 10." The term "about" may refer to plus or minus 10% of the indicated number. For example, "about 10%" may indicate a range of 9% to 11%, and "about 1" may mean from 0.9-1.1.

The present application refers to two dosages differing by "at least one order of magnitude." Two numbers differ by at least one order of magnitude if the quotient of the larger number divided by the smaller number is a value of at least 10.

The present disclosure is directed to a cell-based potency assay including a neuronal network, and to a microelectrode array (MEA) that measures the network's electrophysiological response. Generally, the neuronal network of cells is exposed to a neurotoxic agent, such as BoNT. The assay is capable of detecting BoNTs or BoNT activity with an improved sensitivity over known in vitro methods. The present disclosure provides an assay that demonstrates an improved sensitivity at lower levels of the neurotoxic agent.

As used herein, "BoNT" by itself refers to any or all of the BoNT serotypes (A-G), purified BoNT, purified BoNT in complex, and BoNT in complex.

As used herein, potency is a measure of the strength of a given amount of the neurotoxic agent.

As used herein, a "spike" refers to a spontaneous action potential produced (or fired) by neurons within a network. A mean firing rate (MFR) counts action potentials (spikes) over a predetermined time period in vitro to quantify individual neuron functionality. In one embodiment, the predetermined time period can be one minute (1-min).

As used herein, a "burst" or "bursting" refers to multiple action potentials within a short, time period. Established algorithms detect and quantify burst behavior. A "burst rate" is the number of bursts detected over a predetermined time period, which is contemplated to be one minute (1-min) in some embodiments.

The present disclosure relates to cell-based assays and methods for determining the effect of an agent on the biological activity of a mammalian cell culture. The present disclosure contemplates use of the assays in detecting or measuring the potency of all known BoNT serotypes (A-G) and, more specifically, for BoNT serotype A. However, the disclosure is not limited to BoNT, and is further contemplated for use in connection with other neurotoxic compounds. The cell-based potency assay disclosed herein can be exposed to purified BoNT or BoNT in complex. In one further embodiment, at least one well of an MEA plate can be treated with a dosage of purified BoNT and at least a second well of the MEA plate can be treated with the same dosage of BoNT in complex.

Generally, BoNT affects the proteolytic cleavage of the SNARE protein involved in the signaling of neurons via neurotransmitters. Several steps (cellular binding, uptake, and translocation) of BoNT occur before proteolytic cleavage. Therefore, the cells and/or networks of the contemplated assay should be capable of all steps involved in BoNT toxicity, including SNARE cleavage. The present disclosure contemplates the assay will be based on cells obtained from cortical neuronal cultures, hippocampal neuronal cultures, or a combination of the both. However, embodiments are contemplated that can employ spinal cell cultures, stem-cell cultures, or any combination of cells from a mammalian nervous system including the brain. The present disclosure further contemplates a mammalian neuronal culture, particularly a fresh or frozen primary rodent neuronal culture and, in a more preferred embodiment, a frozen primary rodent neuronal culture.

As discussed supra, the cortical neurons are cultured on a microelectrode array (MEA) plate(s). When the cultures have matured—that is, the synaptic activity peaks in the networks—they are treated with the neurotoxic agent for an exposure period. One embodiment contemplates a maintenance period of about 2 weeks to about 4 weeks for the cultures to mature. The culture is then exposed to a dosage of the neurotoxic agent. The dosage can vary from about 0.1 picomolar (pM) to about 1,000 pM. In another embodiment, the wells of the MEA can be exposed to at least two different dosages of the neurotoxic agent, with each dosage being from about 0.1 pM to about 1,000 pM, more preferably from about 0.10 pM to about 750 pM and, more preferably from about 0.50 pM to about 500 pM, and most preferably from about 0.50 pM to about 50 pM. In one embodiment, the cultures are exposed to at least two dosages of the neurotoxic agent from about 0.10 pM to about 500 pM, more preferably from about 0.50 pM to about 50 pM, and most preferably from about 0.50 pM to about 5.0 pM. At least one of the dosage amounts should be zero, whereby a network having the zero exposure can function as a control.

Desirably, the electrophysiological responses of the cell-based assay are sensitive to the neurotoxic agent exposure, and different dosages of the neurotoxic agent should evoke quantifiably different responses across the networks. In contemplated embodiments, the cell cultures evoke electrophysiological responses, which are sensitive to BoNT exposures of at least 500 pM or less and, more preferably to exposures of at least 50 pM or less. In some embodiments, the cell cultures are sensitive to BoNT exposures from about 0.10 pM to about 500 pM and, more specifically from about 0.50 pM to 50 pM. In other contemplated embodiments, a culture is selected which evokes a wMFR that is sensitive to BoNT exposures of at least 500 pM or less and, more preferably of at least 50 pM or less and, more preferably of at least 5.0 pM or less and, most preferably, of at least 0.5 pM or less.

One aspect of the present disclosure is an MEA that is capable of simultaneously providing up to five replicates of up to five treatment conditions on a single MEA plate. For example, the wells of the MEA plate can be exposed to various combinations of neurotoxic agent and dosages.

After the cell cultures are treated with the neurotoxic agent, the cell culture plates are incubated for the exposure period to allow for the neurotoxic agent to take effect on the cell culture. In embodiments, the exposure period is at least one hour. In other embodiments, the exposure period is at least one day and, in preferred embodiments, the exposure period is at least forty-eight (48) hours. In some embodiments, the electrophysiological activity and/or responses of the cell culture networks can be monitored during the exposure period.

When the exposure period expires, electrophysiological activities are measured across the cell culture networks. These activities can include a spike count (i.e., number of spikes); a mean firing rate (i.e., an average number of spikes per minute); a weighted mean firing rate; a burst count (number of bursts); a mean bursting rate (i.e., an average number of bursts per minute); or a combination of these activities. In preferred embodiments, at least two electrophysiological activities are measured. For example, the wMFR and the burst count are measured. In preferred embodiments, at least the wMFR is measured. The wMFR normalizes the mean firing rate within a well based on the number of active electrodes in the well recording more than a predetermined number of spikes (e.g., 5) per minute. More specifically, a wMFR can be computed for each well on the cell culture plate.

The electrophysiological metrics or responses evoked by the different neurotoxic exposures are then compared to each other to determine a potency of the neurotoxic agent. Desirably, the potency of the neurotoxic agent is dose-dependent.

The present disclosure is also directed to a kit for determining the potency of a neurotoxic agent on the biological activity of a mammalian cell culture. More specifically, the kit includes a mammalian cell culture which is grown on a microelectrode array (MEA) plate. Desirably, the mammalian cell culture is sensitive to BoNT exposures of 0.50 pM or less, as evidenced by a statistically significant reduction in the number of bursts observed over one minute, when compared to control conditions.

The methods of the present disclosure have been tested using botulism neurotoxin (BoNT). In particular, they have been tested using both a purified BoNT serotype and a BoNT serotype in complex.

One aspect of the present disclosure is an in vitro assay that is capable of replacing the murine $LD_{50}$-assay. Another aspect of the disclosure is an in vitro assay that demonstrates at least the same sensitivity and throughput as the $LD_{50}$-assay. The in vitro assay disclosed herein reduces the costs associated with the murine $LD_{50}$-assay by eliminating repetition on live mammals, which can total to 5,000-10,000 rodents a year for a laboratory employing the $LD_{50}$-assay in its operation.

Another aspect of the present disclosure is to provide an in vitro assay that reduces an inherent variability associated with mammalian assays, and reduces the need for live animals. By this, the in vitro assays disclosed herein provide a more controlled testing environment.

A further aspect of the present disclosure is to provide a cell-based potency assay that improves sensitivity in electrophysiological activity within MEA cultures, particularly when exposed to BoNT serotypes.

Another aspect of the present disclosure is to provide in vitro assay that can measure and validate the potency of a neurotoxic agent (such as BoNT) for therapeutic activity, specifically by detecting and confirming safe dosage levels. Another aspect of the present disclosure is to provide an in vitro assay that can measure and validate the recovery of network activity after neurotoxin exposure, specifically by measuring the efficacy of countermeasures (such as test treatments) against neurotoxin exposure. The in vitro assay disclosed herein can be used to determine the potency of BoNT pharmaceuticals and therapeutics for lot release.

The in vitro assay disclosed herein is not limited to any one BoNT serotype; it can used across serotypes, and is further contemplated for use in connection with other neurotoxins, neurotoxic chemicals and compounds.

The following examples are provided to illustrate the assays and methods of the present disclosure. The examples are merely illustrative and are not intended to limit the disclosure to the materials, conditions, or process parameters set forth therein.

EXAMPLES

Example 1

A cell culture was conducted using the cortical and hippocampal neurons of rodents that were exposed to purified BoNT/A and BoNT/A in complex at 50 pM and 500 pM. Neuron cells were cultured from the combined hippocampus cortex and ventricular zone (Brain Bits, LLC, Springfield, Ill.) of fresh embryonic day eighteen (18) rodent brain. The disassociated neurons were cultured for approximately three (3) weeks on multiwall microelectrode array (MEA) plates available through Axion BioSystems of Atlanta, Ga. During the period of culture maintenance and intoxication, cells were monitored using a Maestro MEA system (Axion BioSystems) to ensure maturation of the culture. Each plate contains 48 wells, and each well contains 16 electrodes that record extracellular voltage changes that occur during the firing of action potentials by the cells. The temperature of the plates was maintained at 37° C. during the recordings. The maturation was confirmed when the cultures exhibited adequate levels of electrophysiological activity—i.e., a consistent network MFR and burst phenotype indicative of established synapses. The baseline measurements taken prior to the BoNT/A exposure showed no significant difference in electrophysiological activity (in 1 minute) between the wells for the cell culture. After the culture maintenance period, the cells were exposed to either purified BoNT/A (Metabiologics, Inc., Madison, Wis.) or to BoNT/A in complex at either 50 pM or 500 pM. Cultures serving as a control received no BoNT treatment.

The treated cultures were exposed to BoNT/A for a period of 48 hours, and the electrophysiological activity was evaluated after the 48-hour exposure period. The MEA system recorded spontaneous activity of the network at one minute intervals. The recorded values were used in a one-way analysis of variance (ANOVA) followed by a Dunnett's Multiple Comparison Test to compare the means of the treatment wells to that of the control wells. For each electrophysiological metric considered, an error was computed as equaling the standard error of the mean. After the 48-hour exposure to BoNT/A, significant and quantifiable reductions in electrophysiological activity were observed in the cells.

FIG. 1A is a bar graph comparing the weighted mean firing rate (wMFR) of fresh primary rodent cortical and hippocampal neuronal cultures exposed to pure BoNT/A and BoNT/A in complex at 50 pM and 500 pM. As illustrated in the graph, the wMFR (Hz) evoked from the control culture at the 48-hour time point indicated that the control culture was still exhibiting consistent and reliable spike activity. However, the wMFR was significantly reduced for cultures exposed to BoNT. The wMFRs observed in the intoxicated cultures were less than 50% of that in the control culture, and the wMFRs observed in the cultures exposed to purified BoNT were approximately 25% of that in the control culture. The cultures exposed to purified BoNT exhibited a wMFR that is slightly less than the cultures exposed to BoNT in complex.

FIG. 1B is a bar graph comparing the number of bursts of fresh primary rodent cortical and hippocampal neuronal cultures exposed to pure BoNT/A and BoNT/A in complex at 50 pM and 500 pM. As illustrated in the graph, the number of bursts evoked from the control culture at the 48-hour time point indicated that the control culture was still exhibiting consistent and reliable bursting. However, a complete absence of bursting was observed in the cultures (D, E) that were treated with 500 pM BoNT, and a near complete absence of bursts was observed in cultures (B, C) that were treated with 50 pM of BoNT.

The results indicate that the electrophysiological response to BoNT is not dosage or concentration dependent. The weighted mean firing rate and the number of bursts were approximately the same in cultures exposed to 50 pM of purified BoNT/A and cultures exposed to 500 pM of purified BoNT/A. Further supporting that responses are not dosage-dependent, the wMFR and the number of bursts were approximately the same in cultures exposed to 50 pM of BoNT/A in complex and cultures exposed to 500 pM BoNT/A in complex.

For this example, a change in electrophysiological activity between experimental groups exposed to BoNT and the control was interpreted as a cell type being sensitive to BoNT/A exposure. Therefore, the results indicate that fresh primary rodent cortical and hippocampal neuronal cultures are sensitive to BoNT/A exposure at 50 pM and 500 pM. This lack of apparent differences in electrophysiological activity between the two dosage groups suggests that BoNT/A at 50 pM may approach and/or be at the upper limit of the assay's range with these cell types.

FIG. 1A and FIG. 1B further indicate that the neurons continue to fire action potentials—albeit in diminished numbers—but no longer in short time periods after 48 hours exposure to BoNT. Although the wMFR of intoxicated cultures is substantially diminished, it is not absent. Accordingly, the results indicate that some form of neuronal signaling continues after 48 hours exposure.

Example 2

A cell culture was conducted using the cortical neurons of rodents that were exposed to pure BoNT/A and BoNT/A in complex at 50 pM and 500 pM. Neuron cells were cultured from the cortex of frozen postnatal rodent brain (Lonza, Basel, Switzerland). The disassociated neurons were cultured for approximately 4 weeks on microelectrode array (MEA) plates available through Axion BioSystems of Atlanta, Ga. During the period of culture maintenance and intoxication, cells were monitored using a Maestro MEA system (Axion BioSystems) to ensure maturation of the culture. Each plate contains 48 wells, and each well contains 16 electrodes that record extracellular voltage changes that occur during the firing of action potentials by the cells. The temperature of the plates was maintained at 37° C. during the recordings. The maturation was confirmed when the cultures exhibited adequate levels of electrophysiological activity—i.e., a consistent network MFR and burst phenotype indicative of established synapses. The baseline measurements taken prior to the BoNT/A exposure showed no significant difference in electrophysiological activity (in 1 minute) between the wells for this cell culture. After the culture maintenance period, the cells were exposed to either purified BoNT/A (Metabiologics, Inc., Madison, Wis.) or to BoNT/A in complex at either 50 pM or 500 pM. Cultures serving as a control received no BoNT treatment.

The treated cultures were exposed to BoNT/A for a period of 48 hours, and the electrophysiological activity was evaluated after the 48-hour exposure period. The MEA system recorded spontaneous activity of the network at one minute intervals. The recorded values were used in a one-way analysis of variance (ANOVA) followed by a Dunnett's Multiple Comparison Test to compare the means of the multiple wells. For each electrophysiological metric considered, an error was computed as equaling the standard error of the mean. After the 48-hour exposure to BoNT/A, significant and quantifiable reductions in electrophysiological activity were observed in the cells.

FIG. 2A is a bar graph comparing the weighted mean firing rate of frozen primary rodent cortical neuronal cultures exposed to pure BoNT/A and BoNT/A in complex at 50 pM and 500 pM. As illustrated in the graph, the wMFR (Hz) evoked from the control culture at the 48-hour time point indicated that the control culture was still exhibiting consistent and reliable spike activity. However, the wMFR was significantly reduced for cultures exposed to BoNT/A. The wMFRs observed in the intoxicated cultures approached 50% of that in the control culture, with the greatest reduction being observed in the culture exposed to 500 pM of purified BoNT/A. The cultures exposed to purified BoNT/A exhibited a wMFR that was slightly less than the cultures exposed to BoNT/A in complex.

FIG. 2B is a bar graph comparing the number of bursts of frozen primary rodent cortical neuronal cultures exposed to pure BoNT/A and BoNT/A in complex at 50 pM and 500 pM. As illustrated in the graph, the number of bursts evoked from the control culture at the 48-hour time point indicated that the control culture was still exhibiting consistent and reliable bursting. However, an absence of bursting was observed in the cultures (B, D) that were treated with purified BoNT/A, and a near complete absence in bursting was observed in cultures (C, E) that were treated with BoNT/A in complex.

The results indicate that there is no apparent difference in the electrophysiological responses between frozen primary rodent cortical neuronal cultures exposed to purified BoNT/A and those exposed to BoNT/A in complex. The results indicate that the electrophysiological responses to BoNT/A is not dosage or concentration dependent in cultures treated with BoNT/A in complex, but the wMFR may be dosage or concentration dependent in cultures treated with purified BoNT/A. The results suggest that cultures exposed to 50 pM and 500 pM BoNT/A have similar effects. This suggests that BoNT/A at 50 pM may approach or be at the upper limit of the assay's range for these cell types.

For this example, a change in electrophysiological activity between experimental groups exposed to BoNT and the control was interpreted as a cell type being sensitive to BoNT/A exposure. Therefore, the results indicate that frozen primary rodent cortical neuronal cultures are sensitive to BoNT/A exposures at 50 pM and 500 pM.

Figure 1:
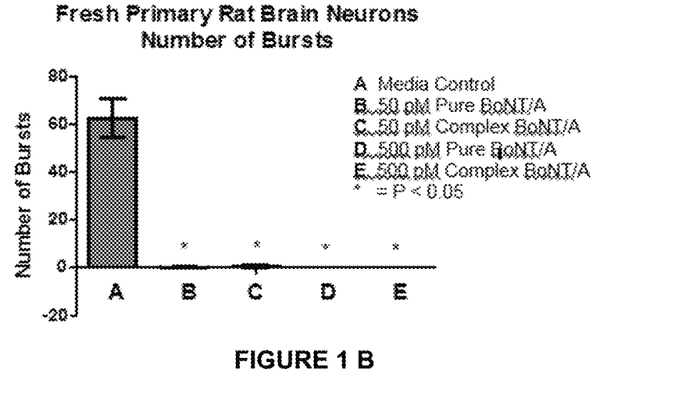
FIG. 1A is a bar graph comparing the weighted mean firing rate of fresh primary rodent cortical and hippocampal neuronal cultures exposed to pure BoNT/A and BoNT/A in complex at 50 pM and 500 pM. A is the control, B and C are exposed to 50 pM, and D and E are exposed to 500 pM.
FIG. 1B is a bar graph comparing the number of bursts of fresh primary rodent cortical and hippocampal neuronal cultures exposed to pure BoNT/A and BoNT/A in complex at 50 pM and 500 pM. A is the control, B and C are exposed to 50 pM, and D and E are exposed to 500 pM.
Figure 1A:
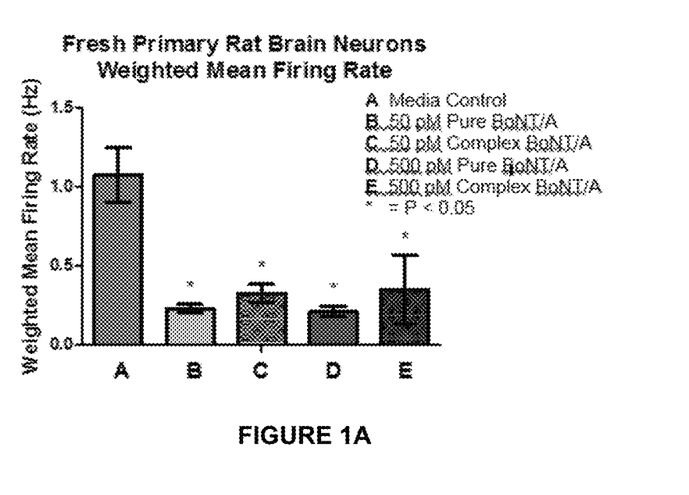
Figure 2A:
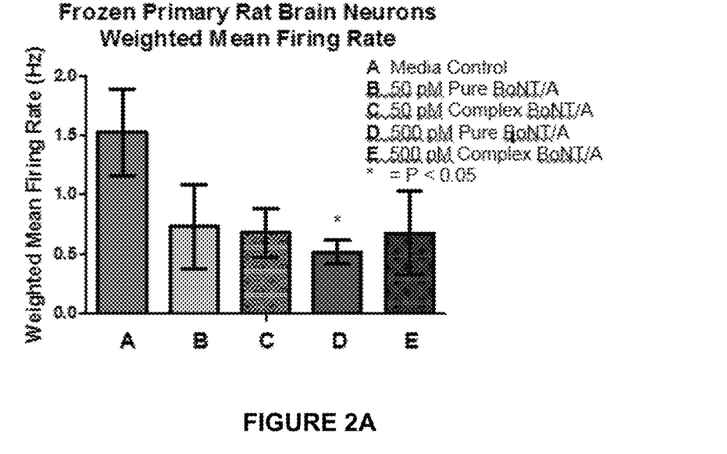
FIG. 2A is a bar graph comparing the weighted mean firing rate of frozen primary rodent cortical neuronal cultures exposed to pure BoNT/A and BoNT/A in complex at 50 pM and 500 pM. A is the control, B and C are exposed to 50 pM, and D and E are exposed to 500 pM.
Figure 2B:
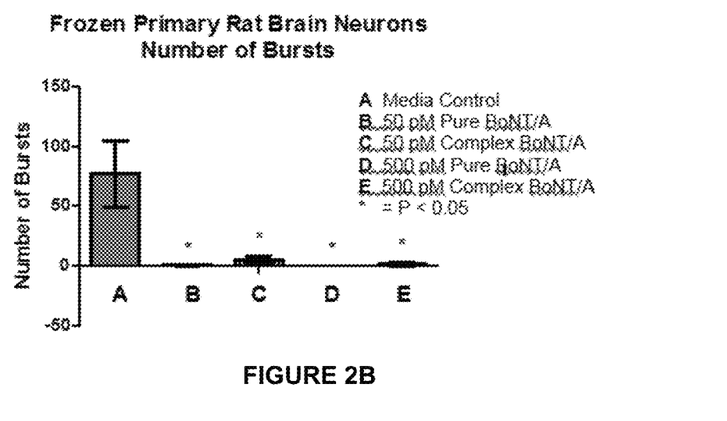
FIG. 2B is a bar graph comparing the number of bursts of frozen primary rodent cortical neuronal cultures exposed to pure BoNT/A and BoNT/A in complex at 50 pM and 500 pM. A is the control, B and C are exposed to 50 pM, and D and E are exposed to 500 pM.

FIG. 2A and FIG. 2B indicate that the neurons continue to fire action potentials—albeit in diminished numbers—but no longer in short time periods after 48 hours exposure to BoNT/A. Although the wMFR of intoxicated cultures is substantially diminished, it is not absent. Accordingly, the results indicate that some form of neuronal signaling continues after 48 hours exposure.

Example 3

A cell culture was conducted using the cortical and hippocampal neurons of rodents that were exposed to pure BoNT/A at 0.50 pM to 500 pM. Neuron cells were cultured from the combined hippocampus cortex and ventricular zone (Brain Bits, LLC, Springfield, Ill.) of fresh embryonic day eighteen (18) rodent brain. The disassociated neurons were cultured for approximately 3 weeks on microelectrode array (MEA) plates available through Axion BioSystems of Atlanta, Ga. During the period of culture maintenance and intoxication, cells were monitored using a Maestro MEA system (Axion BioSystems) to ensure maturation of the culture. Each plate contains 48 wells, and each well contains 16 electrodes that record extracellular voltage changes that occur during the firing of action potentials by the cells. The temperature of the plates was maintained at 37° C. during the recordings. The maturation was confirmed when the cultures exhibited adequate levels of electrophysiological activity—i.e., a consistent network MFR and burst phenotype indicative of established synapses. The baseline measurements taken prior to the BoNT/A exposure showed no significant difference in electrophysiological activity (in 1 minute) between the wells for this cell culture. After the culture maintenance period, the cells were exposed to purified BoNT/A (Metabiologics, Inc., Madison, Wis.) at concentrations ranging from 0.50 pM to 500 pM. Cultures serving as a control received no BoNT treatment.

The treated cultures were exposed to BoNT/A for a period of 48 hours, and the electrophysiological activity was evaluated after the 48-hour exposure period. The MEA system recorded spontaneous activity of the network at one minute intervals. The recorded values were used in a one-way analysis of variance (ANOVA) followed by a Dunnett's Multiple Comparison Test to compare the means of the multiple wells. For each electrophysiological metric considered, an error was computed as equaling the standard error of the mean. After a 48-hour exposure to BoNT/A, some of the wells showed no spontaneous activity. The wMFR computation negated wells with no activity while the bursting count recorded a zero burst value for the wells. For the remaining wells, quantifiable reductions in electrophysiological activity were observed in the network.

Figure 3A:
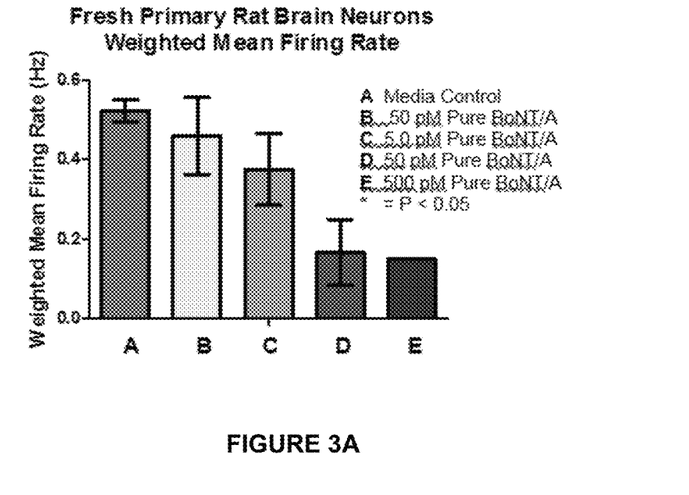
FIG. 3A is a bar graph comparing the weighted mean firing rate of fresh primary rodent cortical and hippocampal neuronal cultures exposed to pure BoNT/A at concentrations between 0.50 pM and 500 pM. A is the control, B is exposed to 0.50 pM, C is exposed to 5.0 pM, D is exposed to 50 pM, and E is exposed to 500 pM.

FIG. 3A is a bar graph comparing the weighted mean firing rate of fresh primary rodent cortical and hippocampal neuronal cultures exposed to pure BoNT/A at concentrations between 0.50 pM and 500 pM. As illustrated in the graph, the wMFR (Hz) evoked from the control culture at the 48-hour time point indicated that the control culture was still exhibiting consistent and reliable spike activity. Reductions in the wMFR were observed for cultures exposed to the BoNT/A, with the greatest reduction being observed in the cultures exposed to purified BoNT/A at 50 pM or more. However, the reductions were not statistically significant.

Figure 3B:
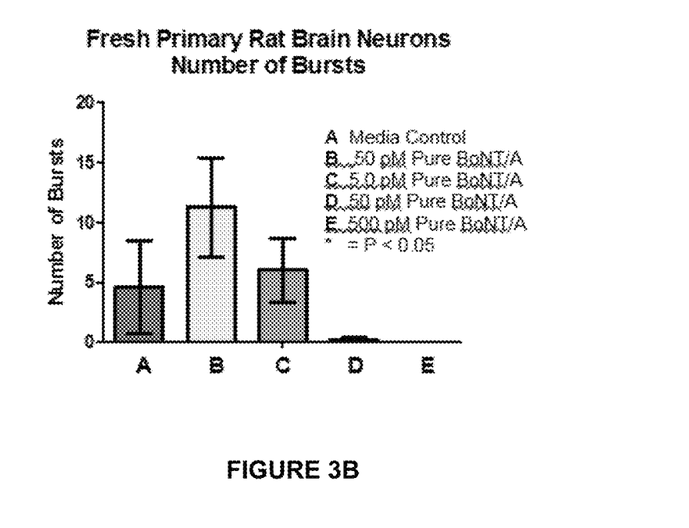
FIG. 3B is a bar graph comparing the number of bursts of fresh primary rodent cortical and hippocampal neuronal cultures exposed to pure BoNT/A at concentrations between 0.50 pM and 500 pM. A is the control, B is exposed to 0.50 pM, C is exposed to 5.0 pM, D is exposed to 50 pM, and E is exposed to 500 pM.

FIG. 3B is a bar graph comparing the number of bursts of fresh primary rodent cortical and hippocampal neuronal cultures exposed to pure BoNT/A at concentrations between 0.50 pM and 500 pM. As illustrated in the graph, the number of bursts evoked from the control culture at the 48-hour time point indicated that the control culture was still exhibiting consistent and reliable bursting. However, no significant reductions in bursting were observed for cultures (B, C) exposed to the purified BoNT/A at 5 pM or less. Indeed, these cultures (B, C) evoked greater bursting behavior. However, an absence of bursting was observed in the cultures (D) that were treated with 500 pM purified BoNT/A, and a near complete absence in bursting was observed in cultures (E) that were treated with 50 pM.

FIG. 3A and FIG. 3B indicate that the electrophysiological response to purified BoNT/A may be dosage or concentration dependent. For this example, a change in electrophysiological activity between experimental groups exposed to BoNT and the control was interpreted as a cell type being sensitive to BoNT/A exposure. Therefore, the results indicate that fresh primary rodent cortical and hippocampal neuronal cultures are sensitive to purified BoNT/A exposure.

Example 4

A cell culture was conducted using the cortical neurons of rodents that were exposed to pure BoNT/A at 0.50 pM to 500 pM. Neuron cells were cultured from the cortex of frozen postnatal rodent brain (Lonza, Basel, Switzerland). The disassociated neurons were cultured for approximately 4 weeks on microelectrode array (MEA) plates available through Axion BioSystems of Atlanta, Ga. During the period of culture maintenance and intoxication, cells were monitored using a Maestro MEA system (Axion BioSystems) to ensure maturation of the culture. Each plate contains 48 wells, and each well contains 16 electrodes that record extracellular voltage changes that occur during the firing of action potentials by the cells. The temperature of the plates was maintained at 37° C. during the recordings. The maturation was confirmed when the cultures exhibited adequate levels of electrophysiological activity—i.e., a consistent network MFR and burst phenotype indicative of established synapses. The baseline measurements taken prior to the BoNT/A exposure showed no significant difference in electrophysiological activity (in 1 minute) between the wells for this cell culture. After the culture maintenance period, the cells were exposed to purified BoNT/A (Metabiologics, Inc., Madison, Wis.) at concentrations ranging from 0.50 pM to 500 pM. Cultures serving as a control received no BoNT treatment.

The treated cultures were exposed to BoNT/A for a period of 48 hours, and the electrophysiological activity was evaluated after the 48-hour exposure period. The MEA system recorded spontaneous activity of the network at one minute intervals. The recorded values were used in a one-way analysis of variance (ANOVA) followed by a Dunnett's Multiple Comparison Test to compare the means of the multiple wells. For each electrophysiological metric considered, an error was computed as equaling the standard error of the mean. After a 48-hour exposure to BoNT/A, significant and quantifiable reductions in electrophysiological activity were observed in the cells.

Figure 4A:
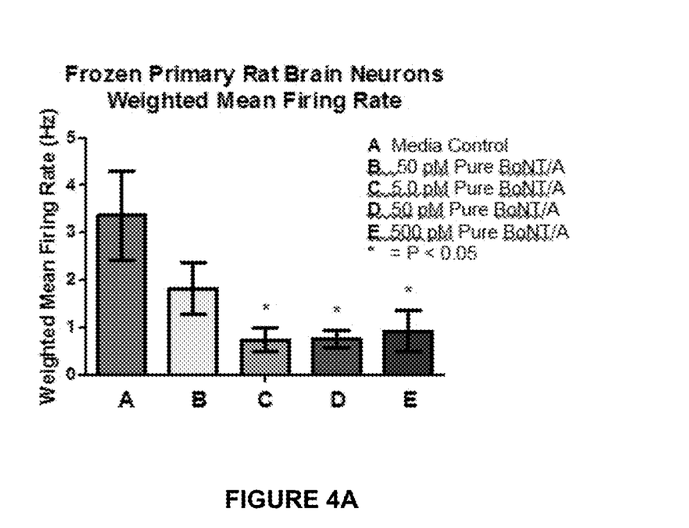
FIG. 4A is a bar graph comparing the weighted mean firing rate of frozen primary rodent cortical neuronal cultures exposed to pure BoNT/A at concentrations between 0.50 pM and 500 pM. A is the control, B is exposed to 0.50 pM, C is exposed to 5.0 pM, D is exposed to 50 pM, and E is exposed to 500 pM.

FIG. 4A is a bar graph comparing the weighted mean firing rate of frozen primary rodent cortical neuronal cultures exposed to pure BoNT/A at concentrations between 0.50 pM and 500 pM. As illustrated in the graph, the wMFR (Hz) evoked from the control culture at the 48-hour time point indicated that the control culture was still exhibiting consistent and reliable spike activity. Statistically significant reductions in the wMFR were observed across all cultures (C-E) exposed to the purified BoNT/A at 5 pM or more.

Figure 4B:
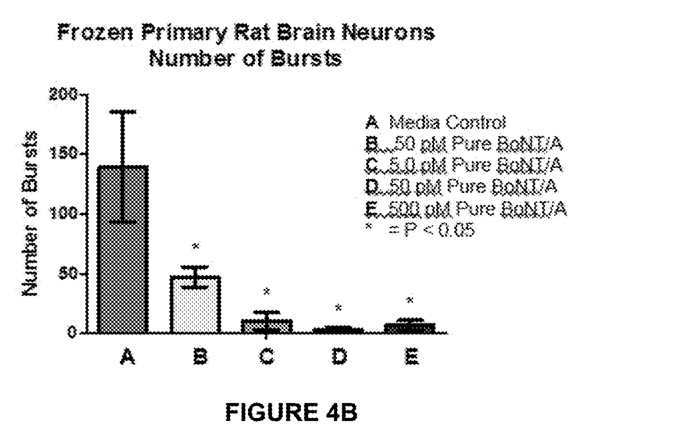
FIG. 4B is a bar graph comparing the number of bursts of frozen primary rodent cortical cultures exposed to pure BoNT/A at concentrations between 0.50 pM and 500 pM. A is the control, B is exposed to 0.50 pM, C is exposed to 5.0 pM, D is exposed to 50 pM, and E is exposed to 500 pM.

FIG. 4B is a bar graph comparing the number of bursts of frozen primary rodent cortical cultures exposed to pure BoNT/A at concentrations between 0.50 pM and 500 pM. As illustrated in the graph, the number of bursts evoked from the control culture at the 48-hour time point indicated that the control culture was still exhibiting consistent and reliable bursting. Statistically significant reductions in bursting were observed across all intoxicated cultures (B-E) exposed to the purified BoNT/A.

FIG. 4A and FIG. 4B indicate that the electrophysiological response to purified BoNT/A may not be dosage or concentration dependent at concentrations above 50 pM; however, FIG. 4A indicates a dosage-dependent effect between 0.5 pM and 5.0 pM of purified BoNT/A and FIG. 4B indicates a dosage dependent effect between 0.5 pM and 50 pM of purified BoNT/A. For this example, a change in electrophysiological activity between experimental groups exposed to BoNT and the control was interpreted as a cell type being sensitive to BoNT/A exposure. Therefore, the results indicate that frozen primary rodent cortical neuronal cultures may be sensitive to purified BoNT/A exposure between 0.5 pM and 50 pM.

SUMMARY OF RESULTS

Purified BoNT/A and BoNT/A in complex resulted in statistically significant reductions in wMFR and number of bursts. All of the treated cultures, supra, demonstrate some sensitivity to BoNT/A exposure. The results indicate that frozen primary rodent cortical neuronal cultures are more sensitive to BoNT/A exposure than fresh primary rodent cortical and hippocampal neuronal cultures. The most sensitive measure (dosage-dependent changes) to BoNT/A was observed within the frozen primary rodent cortical neuronal cultures. The frozen primary rodent cortical neuronal cultures demonstrate greater sensitivity to purified BoNT/A than to BoNT/A in complex.

The method disclosed herein improves over other cell based-BoNT potency assays (e.g., Western Blotting methods) because the end points (electrophysiological data) more closely correlate to the results generated by the $LD_{50}$-assay. These endpoints (wMFR; bursting) are not specific to BoNT/A activity and can be used to evaluate additional BoNT serotypes or other neurotoxic compounds.

The present disclosure has been described with reference to exemplary embodiments. Modifications and alterations may occur to others upon reading and understanding the preceding detailed description. It is intended that the present disclosure be construed as including all such modifications and alterations insofar as they come within the scope of the appended claims or the equivalents thereof.

The invention claimed is:

1. A method for determining a potency of an agent, the method comprising:
    applying doses of the same volume and at least two different concentrations of the agent to different wells of a multi-well plate, each well containing a mammalian cell culture upon a microelectrode array (MEA); and
    measuring a change in the electrophysiological responses of the mammalian cell cultures associated with the at least two different concentrations to determine the potency of the agent;
    wherein the mammalian cell culture comprises neurons cultured from the hippocampus of frozen rodent brain.

2. The method of claim 1, wherein the agent is selected from the group consisting of a purified BoNT serotype and a BoNT serotype in complex.

3. The method of claim 1, further comprising:
    growing the mammalian cell culture upon the MEA for at least three weeks before applying the at least two different concentrations of the agent to the multi-well plate.

4. The method of claim 1, wherein the measured electrophysiological responses are selected from the group consisting of a weighted mean firing rate (wMFR); a mean firing rate (MFR); a burst rate; and combinations thereof.

5. The method of claim 1, wherein the mammalian cell cultures are exposed to the at least two different concentrations for an exposure period of at least 24 hours.

6. The method of claim 1, wherein the mammalian cell cultures are exposed to the at least two different concentrations for an exposure period of at least 48 hours.

7. The method of claim 1, wherein the at least two concentrations of the agent are from about 0.10 picomolar to about 500 picomolar (pM).

8. The method of claim 1, wherein the at least two concentrations of the agent are from about 0.10 picomolar to about 50 picomolar (pM).

9. The method of claim 1, wherein the at least two concentrations of the agent are from about 50 picomolar to about 500 picomolar (pM).

10. The method of claim 1, wherein the at least two concentrations of the agent differ by at least one order of magnitude.

11. The method of claim 1, wherein the potency of the agent is also determined by considering the electrophysiological response of a control mammalian cell culture that is not exposed to the agent.

12. A *Clostridium botulinum* neurotoxin (BoNT) assay method comprising:
    applying doses of the same volume and at least two different concentration of BoNT to different wells of a multi-well plate, each well containing a mammalian cell culture upon a microelectrode array (MEA); and
    measuring a change in the electrophysiological responses of the mammalian cell cultures associated with the at least two different concentrations of BoNT;

wherein the mammalian cell culture comprises neurons cultured from the hippocampus of frozen rodent brain.

13. The BoNT assay method of claim 12 further comprising:
  growing the mammalian cell culture upon the MEA for at least three weeks before applying the at least two different concentrations of the agent to the multi-well plate.

14. The BoNT assay method of claim 13, wherein the mammalian cell cultures are exposed to the at least two different concentrations of BoNT for an exposure period of at least 48 hours before measuring the change in electrophysiological activity.

15. The BoNT assay method of claim 14, wherein the measuring includes:
  measuring a change in a weighted mean firing rate (wMFR) of the mammalian cell cultures associated with the at least two different concentrations of BoNT; and
  measuring a change in burst rate of the mammalian cell cultures associated with the at least two different concentrations of BoNT.

16. The BoNT assay method of claim 15, wherein:
  the at least two concentrations of the agent include two concentrations differing by at least one order of magnitude.

* * * * *